United States Patent
Zadno-Azizi et al.

[11] Patent Number: 5,833,644
[45] Date of Patent: Nov. 10, 1998

[54] METHOD FOR EMBOLI CONTAINMENT

[75] Inventors: Gholam-Reza Zadno-Azizi, Newark; Celso J. Bagaoisan, Union City; Ketan P. Muni, San Jose; Jefferey C. Bleam, Boulder Creek, all of Calif.

[73] Assignee: Percusurge, Inc., Sunnyvale, Calif.

[21] Appl. No.: 812,875

[22] Filed: Mar. 6, 1997

Related U.S. Application Data

[63] Continuation-in-part of Ser. No. 650,464, May 20, 1996.

[51] Int. Cl.$^6$ .................................................. A61M 31/00
[52] U.S. Cl. ................................ 604/52; 604/48; 604/101
[58] Field of Search .............................. 604/101, 48, 52, 604/53, 102, 103, 95; 606/159, 194

[56] References Cited

U.S. PATENT DOCUMENTS

| | | | |
|---|---|---|---|
| 4,610,662 | 9/1986 | Weikl et al. ........................... | 604/53 |
| 4,867,742 | 9/1989 | Calderon .................................. | 604/28 |
| 4,911,163 | 3/1990 | Fina ..................................... | 604/101 X |
| 5,250,060 | 10/1993 | Corbo et al. ............................. | 606/159 |
| 5,423,742 | 6/1995 | Theron ..................................... | 604/28 |
| 5,462,529 | 10/1995 | Simpson et al. ........................... | 604/101 |
| 5,484,412 | 1/1996 | Pierpont .................................. | 604/101 |

*Primary Examiner*—Wynn Wood Coggins
*Assistant Examiner*—N. Kent Gring
*Attorney, Agent, or Firm*—Knobbe, Martens, Olson & Bear, LLP

[57] ABSTRACT

A multi-catheter emboli containment system is disclosed in which a treatment chamber within a blood vessel is formed by at least two occlusion balloons on opposite sides of a stenotic lesion, thereby preventing emboli migration during the treatment procedure. Irrigation and aspiration are provided to remove emboli and debris from the chamber. The irrigation and aspiration can be provided through separate catheters, or, the catheters used to create the chamber, together with the catheter used to provide therapy to the stenosis can be used. The catheters are all sized so as to be concentric, slidably disposed with respect to one another, and able to be delivered into blood vessels less than 25 mm in diameter or even smaller.

41 Claims, 12 Drawing Sheets

Flow Rate vs δp

Flow Rate Interaction Plot Between Irrigation and Aspiration Pressures

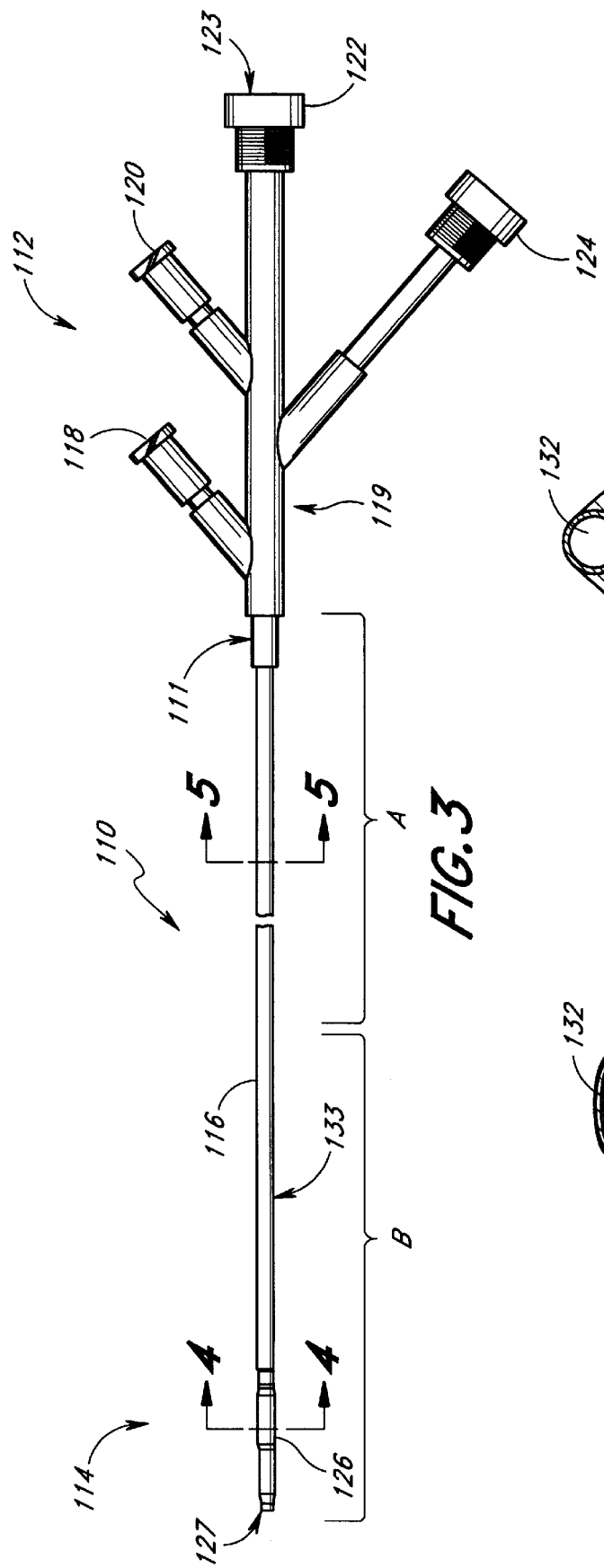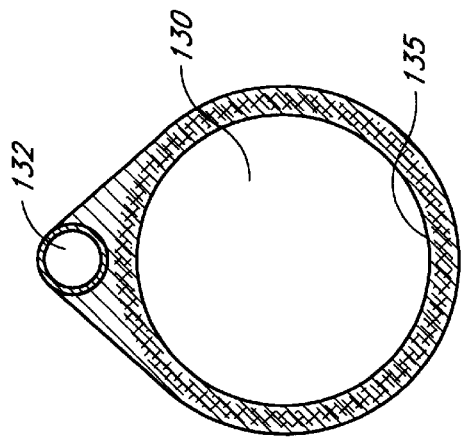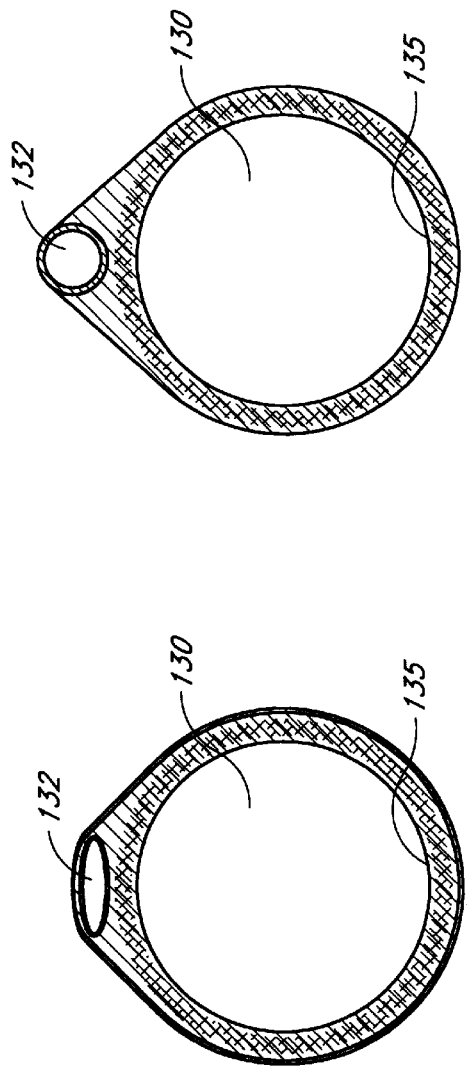

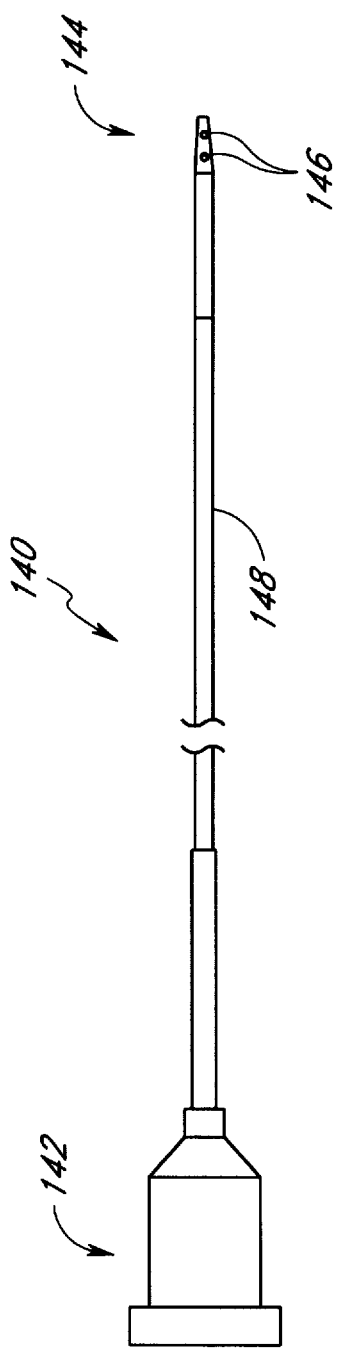

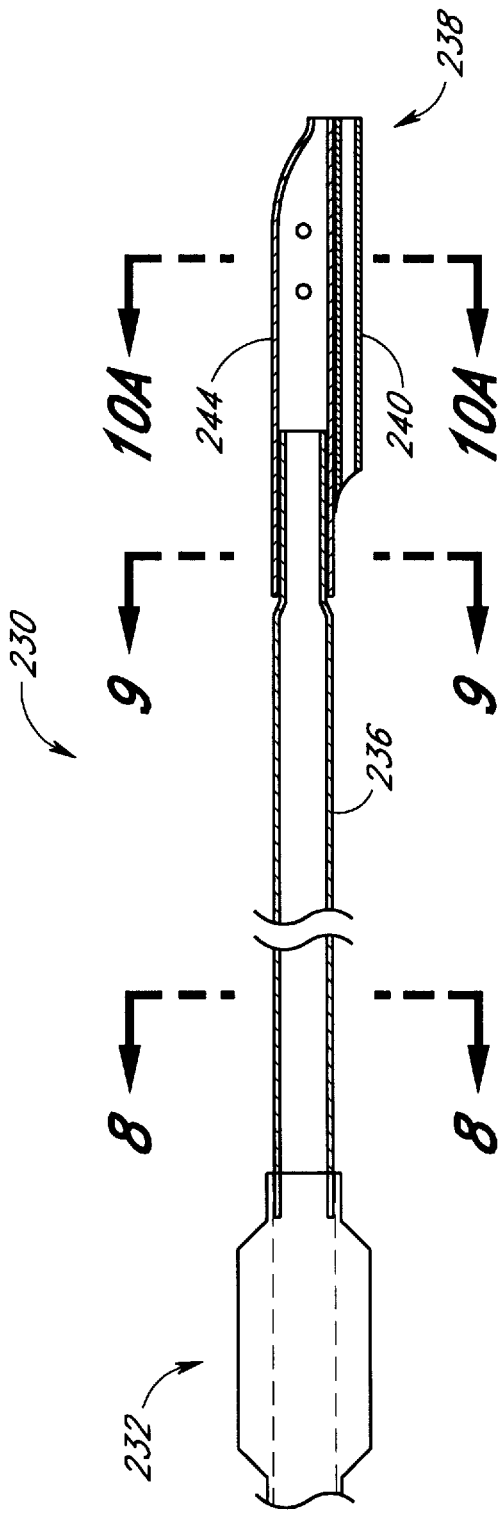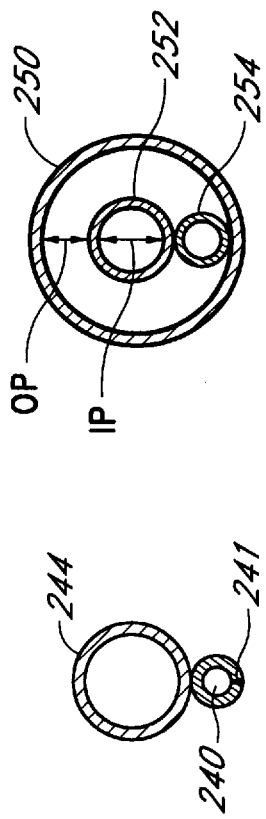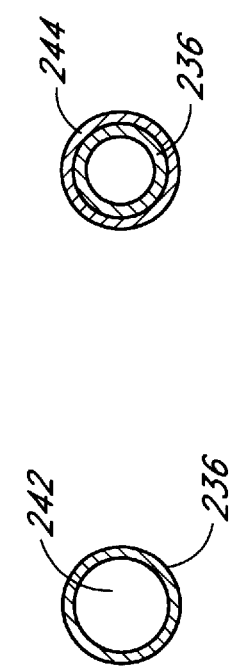

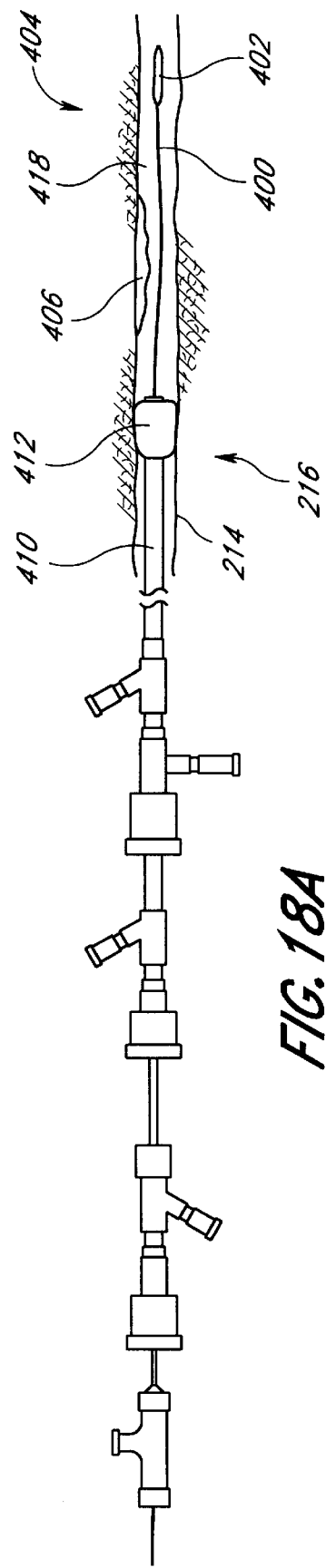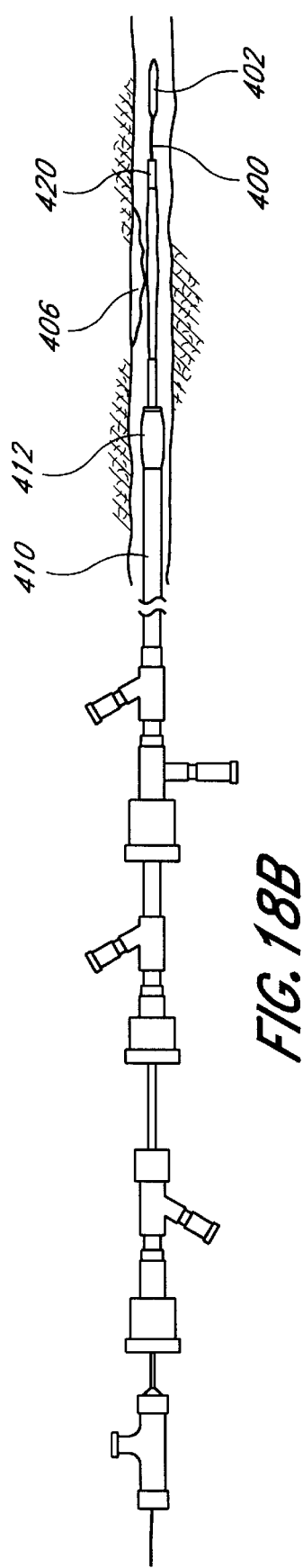

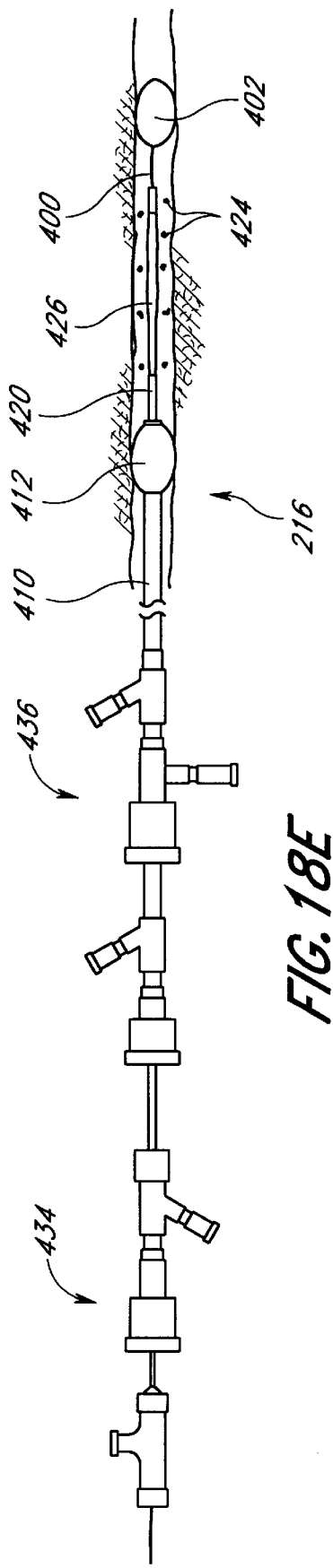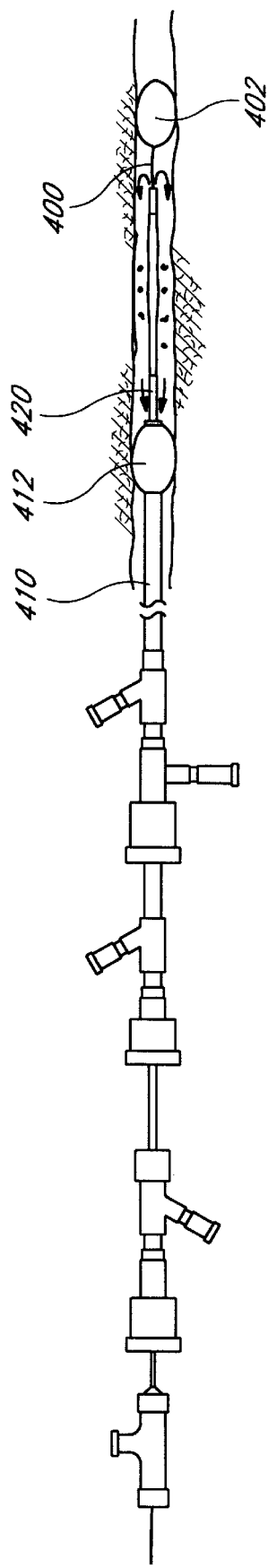
FIG. 18E
FIG. 18F

METHOD FOR EMBOLI CONTAINMENT

CROSS-REFERENCE TO RELATED APPLICATION

This application is a continuation-in-part of U.S. patent application Ser. No. 08/650,464 filed May 30, 1996 pending, the entirety of which is hereby incorporated by reference.

BACKGROUND OF THE INVENTION

1. Field of the Invention

The present invention relates generally to medical devices, and in particular, to a system of improved irrigation and aspiration catheters and methods for treating occlusions within blood vessels and containment of emboli and resulting debris.

2. Description of Related Art

Human blood vessels often become occluded or blocked by plaque, thrombi, other deposits, or emboli which reduce the blood carrying capacity of the vessel. Should the blockage occur at a critical place in the circulatory system, serious and permanent injury, and even death, can occur. To prevent this, some form of medical intervention is usually performed when significant occlusion is detected.

Balloon angioplasty, and other transluminal medical treatments, are well-known, and have been proven efficacious in the treatment of stenotic lesions in blood vessels. The application of such medical procedure to certain blood vessels, however, has been limited, due to the risks associated with creation of emboli during the procedure. For example, angioplasty is not the currently preferred treatment for lesions in the carotid artery, because of the possibility of dislodging plaque from the lesion, which can enter the various arterial vessels of the brain and cause permanent brain damage. Instead, surgical procedures such as carotid endarterectomy are currently used, wherein the artery is split open and the blockage removed, but these procedures present substantial risks.

Other types of intervention for blocked vessels include atherectomy, deployment of stents, introduction of specific medication by infusion, and bypass surgery. Each of these methods are not without the risk of embolism caused by the dislodgement of the blocking material which then moves downstream. In addition, the size of the vessel may limit access to the vessel.

There is therefore a need for an improved emboli containment system and methods of use which decrease the risk of symptomatic embolization and other complications in the patient.

SUMMARY OF THE INVENTION

The present invention advantageously provides an improved irrigation and aspiration system and methods of use in an emboli containment system. A treatment chamber within a blood vessel is created using two or more occlusive devices, one on each side of a stenotic lesion or other occlusion, thereby preventing emboli and debris migration during the treatment procedure. It is to be understood that "occlusion" as used herein, includes both partial and complete occlusions, stenosis, emboli, thrombi, plaque, and any other substance which at least partially occludes the lumen of the blood vessel. By occlusive device is meant any device which is capable of preventing at least some particles or other debris from moving downstream. Examples of occlusive devices include inflatable balloons, filters and the like. Following treatment of the occlusion, irrigation and aspiration are provided either through the annuli between the catheters used to create the containment chamber, or through separate irrigation and aspiration catheters, to remove particles of material freed during the treatment.

The emboli containment procedures of the present invention are advantageous because they permit the clinician to utilize the benefits of transluminal treatment in a wider variety of blood vessels. The design of the catheters included in the present invention makes it easier for the clinician to utilize an emboli containment system, and makes it possible for the system to be used in even very small vessels with diameters of less than 6 mm, as well as vessels as large as 25 mm.

The present invention provides for a method for containing and removing an occlusion within a blood vessel. An adjustable length chamber is first created between two occlusion devices, and irrigation fluid is provided at one end of the chamber while aspiration pressure is provided at the other end of the chamber. The flow into the chamber and the flow out of the chamber is such that the change in pressure inside the chamber does not damage the vessel. Thus, the change in pressure is preferably not more than approximately 50 psi, to avoid damaging the vessel. Proximal aspiration pressures ranging from about −10 to −30 in-Hg and proximal irrigation pressures ranging from about 5 to 30 psig are preferred. The aspiration and irrigation pressures can be provided simultaneously, or in a discontinuous or pulsed fashion. Such a method can be performed in any vessel, including those of less than 25 mm in diameter, and even in vessels as small as 6 mm in diameter or less.

Another aspect of the present invention provides a method for treating an occlusion and containing and removing emboli and debris from within a blood vessel, wherein a main catheter having a first occlusive device on its distal end is advanced through the blood vessel until the occlusive device is proximal to the occlusion. The occlusive device is then activated to occlude the vessel. An inner catheter having a second occlusive device on its distal end is advanced through the blood vessel until the second occlusive device is just distal to the occlusion and the second occlusive device is activated. The main catheter can be an over-the-wire type, wherein the inner catheter is inserted through a main lumen in the main catheter. Alternatively, in a single operator type catheter, the inner catheter is in a separate lumen and only a portion of the main catheter, i.e. the short inner catheter lumen, rides over the inner catheter. In some catheter designs, the inner catheter lumen extends the length of the main catheter.

An intermediate catheter, or at least a portion thereof, is advanced through the blood vessel until the distal end of the catheter is at the site of the occlusion, and therapy is performed using the intermediate or therapy catheter. Following reduction or removal of the occlusion, irrigation fluid is provided at one end of the chamber while aspiration pressure is provided at the other end. The inner catheter and the intermediate catheter are preferably sized to provide an annulus therebetween, so that the irrigation fluid is provided through the annulus. The intermediate catheter and the main catheter can also be sized to provide an annulus therebetween, so that the aspiration pressure is provided through that annulus. Alternatively, aspiration can be provided through the annulus between the inner and intermediate catheters, while irrigation fluid is provided through the annulus between the main and intermediate catheters. This eliminates the need to provide separate aspiration and irrigation catheters.

Following irrigation and aspiration, the intermediate or therapy catheter is removed, the occlusive devices are deactivated, and the inner and main catheters are removed. In preferred embodiments of the invention, the inner catheter is a guidewire having an inflatable balloon on its distal end, and the main catheter also has a balloon as its occlusive device.

Should separate aspiration and irrigation catheters be desired, the therapy catheter is first removed from the chamber following therapy, and an irrigation catheter is advanced until the distal end of the irrigation catheter is positioned within the chamber adjacent the first occlusive device. Irrigation fluid is then provided through the irrigation catheter while aspiration is provided through the pathway created between the irrigation catheter and the main catheter. The change in pressure within the chamber during irrigation and aspiration should not exceed about 50 psi, to avoid damaging the vessel itself. Alternatively, an aspiration catheter can be advanced into the chamber following removal of the therapy catheter, and aspiration provided through the aspiration catheter.

The present invention also includes a method for treating an occlusion and containing and removing emboli and debris from within a blood vessel wherein an inner catheter is delivered first to a site proximal to the occlusion. The main catheter is delivered to a site proximal to the occlusion, and the occlusive device on the main catheter is activated. The occlusive device on the inner catheter is then positioned distal to the occlusion and activated to create a chamber surrounding the occlusion. The occlusive devices are preferably balloons, which can be inflated or mechanically activated to occlude the vessel. Once the chamber is formed, an intermediate catheter is then delivered to the site of the occlusion, therapy is performed, and irrigation and aspiration is provided at either end of the chamber to remove the occlusion and debris resulting from the therapy.

Again, the inner catheter and the intermediate catheter are preferably sized to provide an annulus therebetween, so that the irrigation fluid is provided through the annulus. The intermediate catheter and the main catheter can also be sized to provide an annulus therebetween, so that the aspiration is provided through that annulus. Alternatively, aspiration can be provided through the annulus between the inner and intermediate catheters, while irrigation fluid is provided through the annulus between the main and intermediate catheters. This eliminates the need to provide separate aspiration and irrigation catheters. If desired, however, an irrigation or aspiration catheter or a combination irrigation/aspiration catheter can be supplied after removal of the therapy catheter.

In yet another embodiment of the present invention, the inner catheter is delivered first to a site distal to the occlusion, followed by delivery of the main catheter to a site proximal to the occlusion. The occlusive devices are activated to occlude the vessel and form a containment chamber, then the intermediate catheter is delivered and therapy performed. Irrigation and aspiration are provided to remove the occlusion and debris following therapy.

Still another embodiment of the present invention involves the delivery of a main catheter and activation of its occlusive device, followed by delivery of an inner catheter and activation of its occlusive device to create a chamber surrounding the occlusion. An intermediate catheter is then delivered, and used to treat the occlusion while creating a pressure change within the chamber which does not exceed 50 psi.

Accordingly, the present invention provides for a fast and efficient irrigation and aspiration of an emboli containment chamber. The present methods can eliminate the need for separate irrigation and aspiration catheters, and can be performed in extremely small blood vessels. The methods of the present invention allow the physician to restore normal blood flow in the blood vessel in a very short period of time, while also reducing the risks associated with these types of procedures.

BRIEF DESCRIPTION OF THE DRAWINGS

FIG. 3 is a side view of the main catheter for use in the present invention.

FIG. 4 is a cross-sectional view of the main catheter taken along line 4—4 of FIG. 3.

FIG. 5 is a cross-sectional view of the main catheter taken along line 5—5 of FIG. 3.

FIG. 6 is a side view of an over-the-wire irrigation or aspiration catheter for use in the present invention.

FIG. 7 is a side view of a single operator irrigation catheter for use in the present invention.

FIGS. 8 through 10A are cross-sectional views of the single operator irrigation catheter taken along lines 8—8, 9—9 and 10A—10A of FIG. 7.

FIG. 10B is a cross-sectional view of the single operator irrigation catheter inserted within the main catheter, illustrating schematically the irrigation and aspiration paths which are formed by the catheter system of present invention.

FIGS. 18A–H illustrate the use of the catheters of the present invention in an emboli containment treatment procedure.

DETAILED DESCRIPTION OF THE PREFERRED EMBODIMENT

Figure 1:
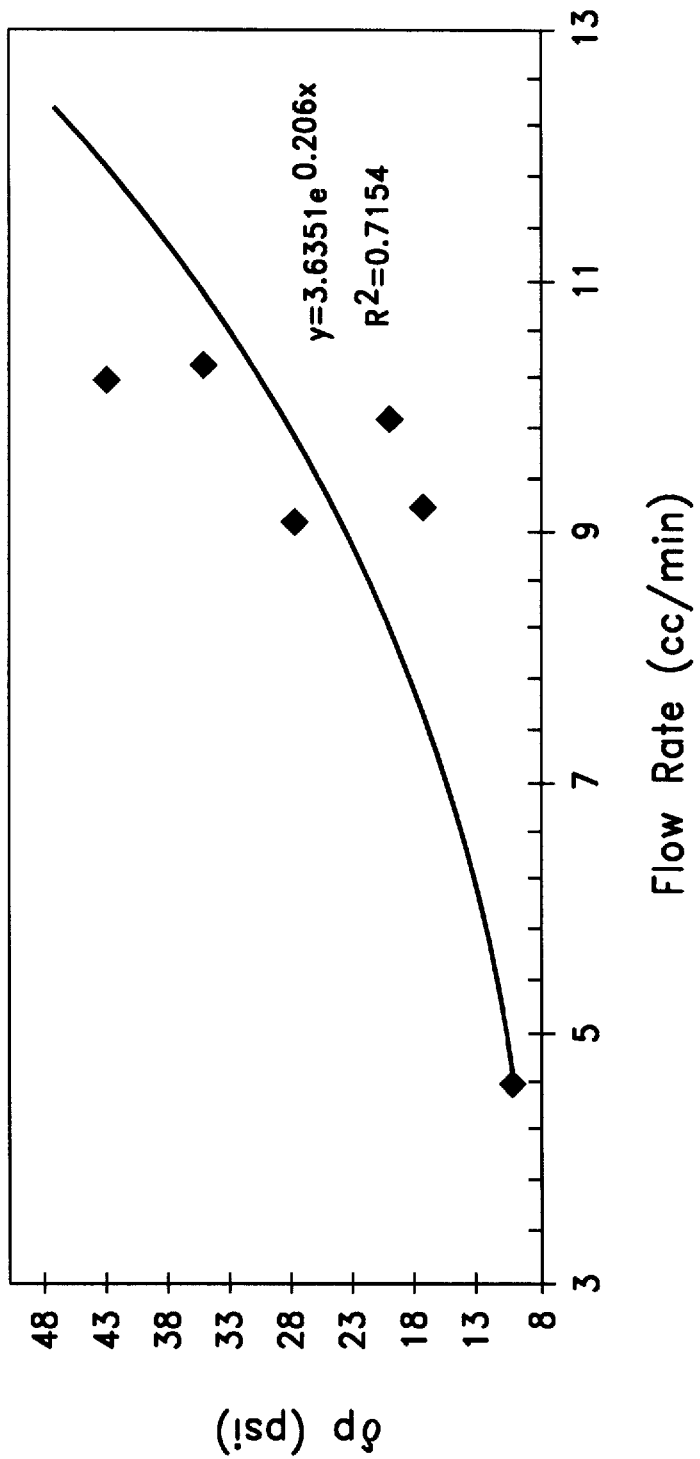
FIG. 1 is a graph illustrating the exponential trend of fluid flow versus pressure in the emboli containment chamber.

The present invention provides a system of improved irrigation and aspiration catheters and methods for treating stenosis or occlusions within blood vessels and emboli particle containment. The methods and apparatus of the present invention are adapted for use in the treatment of a stenosis or an occlusion in a blood vessel in which the stenosis or occlusion has a length and a width or thickness which at least partially occludes the vessel's lumen. As noted above, "occlusion" includes both partial and complete occlusions, stenosis, emboli, thrombi, plaque and any other substance which at least partially occludes the vessel's lumen.

Fluid Mechanics of Irrigation/Aspiration

The effect of the pressure differential between the irrigation and aspiration catheters on the emboli containment chamber was first studied. It was confirmed that as the pressure differential increased, the flow rate in the chamber increased exponentially.

Some preliminary studies demonstrated that the fluid flow through the irrigation catheter into the chamber then out through the aspiration catheter could be represented by equations for fluid flow in pipes. The basic equation for incompressible fluid flow in a pipe is based on Bernoulli's equation for steady state flow of inviscid, incompressible fluids:

$$p_1 + \tfrac{1}{2}\rho V_1^2 + \gamma Z_1 = p_2 + \tfrac{1}{2}\rho V_2^2 + \gamma Z_2$$

where p=pressure, ρ=density, V=velocity, γ=specific weight, and Z=elevation. When fluid flows in a pipe or, in this case the irrigation/aspiration system within the containment chamber, the behavior of the fluid can be described by the equation:

$$\Delta p = K\rho V^2/2 \quad . let K\rho/2 = k_2$$

$$\Delta p = k_2 V^2$$

$$\Delta p \propto V^2$$

where K is the resistance coefficient and the fluid velocity V can be expressed in terms of fluid flow (Q) by the equation V=Q/A where A=cross sectional area. Therefore for a given irrigation/aspiration system K, A and ρ can be assumed to be constant, indicating that the square of the fluid velocity is proportional to the pressure differential between the irrigation and aspiration pressures.

The results of the initial testing clearly showed that the fluid flow through the system did behave as predicted and proved that as the change in pressure (Δp) increased the flow rate increased. The time required to remove emboli from the chamber with respect to the irrigation and aspiration pressures and the cross sectional area used for aspirating was also investigated. As expected, as the aspiration cross sectional area increased, there was a reduction in the time required to remove the emboli which was due to the corresponding fluid flow increase. The results showed that by increasing the initial Δp across the system, the flow rate increased as well, but the irrigation pressure had more effect on the flow rate than the aspiration pressure. The emboli removal was also affected by the flow rate with a shorter time being required for removal for a higher Δp and again, the higher irrigation pressure was the major factor.

There was some initial concern that pressure would build within the chamber if the configuration of the system or the change in pressure was not properly designed. However, in the studies performed, the pressure within the chamber ranged between −7.1 to 2 psig (gauge pressure where 0 psig=atmospheric pressure) depending on the main catheter internal diameter (ID) and the Δp across the system. These results indicate that over pressurization of the chamber is not an issue.

Further investigation into the fluid mechanics in the emboli containment chamber was conducted as follows. A main catheter having an occlusion balloon on its distal end was first inserted into a 4 mm ID flexible polymer tube. A guidewire having a 4 mm inflatable occlusion balloon at its distal end was inserted through the main catheter and past the distal end of the main catheter so that a 100 mm chamber was created between the two balloons within the flexible tube. An irrigation catheter was then positioned just proximal of the guidewire balloon. The main and guidewire balloons were then inflated to isolate the chamber.

A pump was connected to an irrigation port on the irrigation catheter using a stopcock, and a pressure gauge was connected inline with the pump output line. A 60 cc syringe was connected to an aspiration port on the main catheter to provide aspiration pressure or vacuum. A vacuum/pressure gauge was connected inline with the aspiration line to the syringe. A 100 ml beaker of fluid (8.5 g/L sodium chloride solution or water) to be used in the test was then provided. The pump was activated until the chamber was filled with fluid and all the air was out of the irrigation and aspiration catheters.

A summary of the apparatus used in testing is shown below in Table 1:

TABLE 1

Test Apparatus Dimensional Breakdown

| | |
|---|---|
| Main Catheter ID/OD: | .065/.086 |
| Irrigation Catheter ID/OD: | .038/.046 |
| Asp. X-sectional Area: | .0017 in$^2$ |
| Chamber length: | 10 cm |
| Chamber ID: | .4 cm |
| Chamber Volume: | 1.3 cc |

With the input line to the pump in the filled beaker, the pump was activated and adjusted to the desired pressure. Twenty-five cc of fluid was measured and placed into an empty beaker, and the input line to the pump was placed into the beaker. The stopcock to the aspiration catheter was closed, and the plunger on the 60 cc syringe was pulled back until the desired vacuum was obtained. The pump was then turned on, and simultaneously, the stopcock to the aspiration port was opened and a timer was started. When the desired time had passed, the pump was turned off and the fluid remaining in the beaker and the fluid collected in the 60 cc syringe was measured.

A two level factorial design with two replications was used to determine the effect irrigation pressure and aspiration vacuum had on the flow rate through the system via the 4 mm×100 mm tubular chamber (see Table 2).

TABLE 2

| | Factors and levels | |
|---|---|---|
| Factor | Low Level | High Level |
| Irrigation Pressure | 5 psig | 30 psig |
| Aspiration Pressure | −10 in-Hg | −25 in-Hg |

The results of the testing are shown below in Tables 3 and 4.

TABLE 3

Flow Data Using a Saline Solution for Irrigation

| Initial* | Irr | Asp | δVin | | δVout | | δVin−δVout | | Time | | ASP Flow Rate | |
|---|---|---|---|---|---|---|---|---|---|---|---|---|
| δP (psi) | Initial Press (psig) | Initial Press (in-Hg, gauge) | mean (cc) | stdev (cc) | mean (cc) | stdev (cc) | mean (cc) | stdev (cc) | mean (sec) | stdev (sec) | mean (cc/min) | stdev (cc/min) |
| 9.9  | 5  | −10 | 4.2  | .20 | 4.1 | .23  | .2  | .12 | 53.7 | 1.46 | 4.6  | .15 |
| 17.3 | 5  | −25 | 8.3  | .58 | 8.4 | .35  | −.1 | .23 | 54.8 | .37  | 9.2  | .33 |
| 19.9 | 15 | −10 | 9.1  | .12 | 8.8 | .20  | .3  | .31 | 53.2 | 1.04 | 9.9  | .41 |
| 27.3 | 15 | −25 | 10.5 | .46 | 8.4 | .53  | 2.1 | .42 | 55.6 | 2.45 | 9.1  | .65 |
| 34.9 | 30 | −10 | 10.1 | .12 | 9.3 | 9.27 | .8  | .40 | 53.7 | .58  | 10.4 | .36 |
| 42.3 | 30 | −25 | 10.2 | .40 | 9.1 | .61  | 1.1 | .23 | 53.6 | .58  | 10.2 | .57 |

TABLE 4

Flow Data Using Water for Irrigation

| Initial* | Irr | Asp | δVin | | δVout | | δVin−δVout | | Time | | ASP Flow Rate | |
|---|---|---|---|---|---|---|---|---|---|---|---|---|
| δP (psi) | Initial Press (psig) | Initial Press (in-Hg, gauge) | mean (cc) | stdev (cc) | mean (cc) | stdev (cc) | mean (cc) | stdev (cc) | mean (sec) | stdev (sec) | mean (cc/min) | stdev (cc/min) |
| 9.9  | 5  | −10 | 7.3  | .30  | 6.6  | .38  | .7  | .15  | 57.7 | 2.23 | 6.9  | .15 |
| 17.3 | 5  | −25 | 14.4 | 2.09 | 13.4 | 1.43 | 1.0 | 2.15 | 56.1 | .46  | 14.4 | 1.47 |
| 19.9 | 15 | −10 | 12.1 | 4.22 | 9.3  | .58  | 2.8 | 3.64 | 56.0 | .57  | 10.0 | .56 |
| 27.3 | 15 | −25 | 10.5 | .50  | 9.9  | .61  | .6  | .53  | 54.6 | 2.81 | 10.9 | .78 |
| 34.9 | 30 | −10 | 10.9 | 1.01 | 10.1 | .50  | .7  | .76  | 55.5 | 3.41 | 11.0 | .15 |
| 42.3 | 30 | −25 | 9.8  | .35  | 10.0 | .20  | −.2 | .20  | 53.1 | .99  | 11.3 | .15 |

*Pressure equalization after max 45 sec. As δP increases, the time to equalize increases δP is the pressure differential between the irrigation bag and the vacuum in the aspiration syringe
V = volume and n = 3 unless otherwise noted The irrigation pressure was varied between 5 and 30 psig with the aspiration pressure varying between −10 and −25 in-Hg. The results show that there was little difference between the use of the saline solution and the use of water. The lowest flow rate of 4.6 cc/min was obtained for a 5 psi irrigation pressure and a −10 in-Hg aspiration pressure (δp=9.9 psi). The highest flow rates were obtained when a 30 psi irrigation pressure was used with rates of 10.4 and 10.2 cc/min for an aspiration pressure of −10 (δp=34.9 psi) and −25 in-Hg (δp=42.3 psi) respectively.

The results of this two level factorial design supported the results obtained in earlier studies: that as the δp across the system increases, the flow rate increases exponentially.

The results were consistent with Bernoulli's equations for flow in a tube in that the fluid velocity is proportional to the square root of the pressure differential between the two points assuming a constant fluid density and losses. When the flow rate was plotted against δp an exponential trend with an $R^2=0.7154$, the results support the proportional relation between pressure and the fluid flow rate expressed in equation 2 (see FIG. 1).

Analysis of the data produced an extremely significant model with an adjust $R^2=0.994$ (see Table 5). Each of the main factors as well as the interaction between the irrigation and aspiration pressure were highly significant with a p<0.0000.

TABLE 5

Data Analysis and Model for Flow Rate (solution: saline)

| | |
|---|---|
| Adjusted $R^2$ | .994 |
| Standard Error | .227 |
| Mean Abs. Error | .1278 |

TABLE 5-continued

Data Analysis and Model for Flow Rate (solution: saline)

| | Coefficient | Error | Factor* | p-value |
|---|---|---|---|---|
| Flow Rate (cc/min)= | 8.6 | ±.0654 | | |
| | 3.367 | ±.1309 | Irrigation | .0000 |
| | −2.2 | ±.1309 | Aspiration | .0000 |
| | 2.37 | ±.1309 | Irr* Asp | .0000 |

*Use coded values between −1 an 1 to determine predicted flow rates

Figure 2:
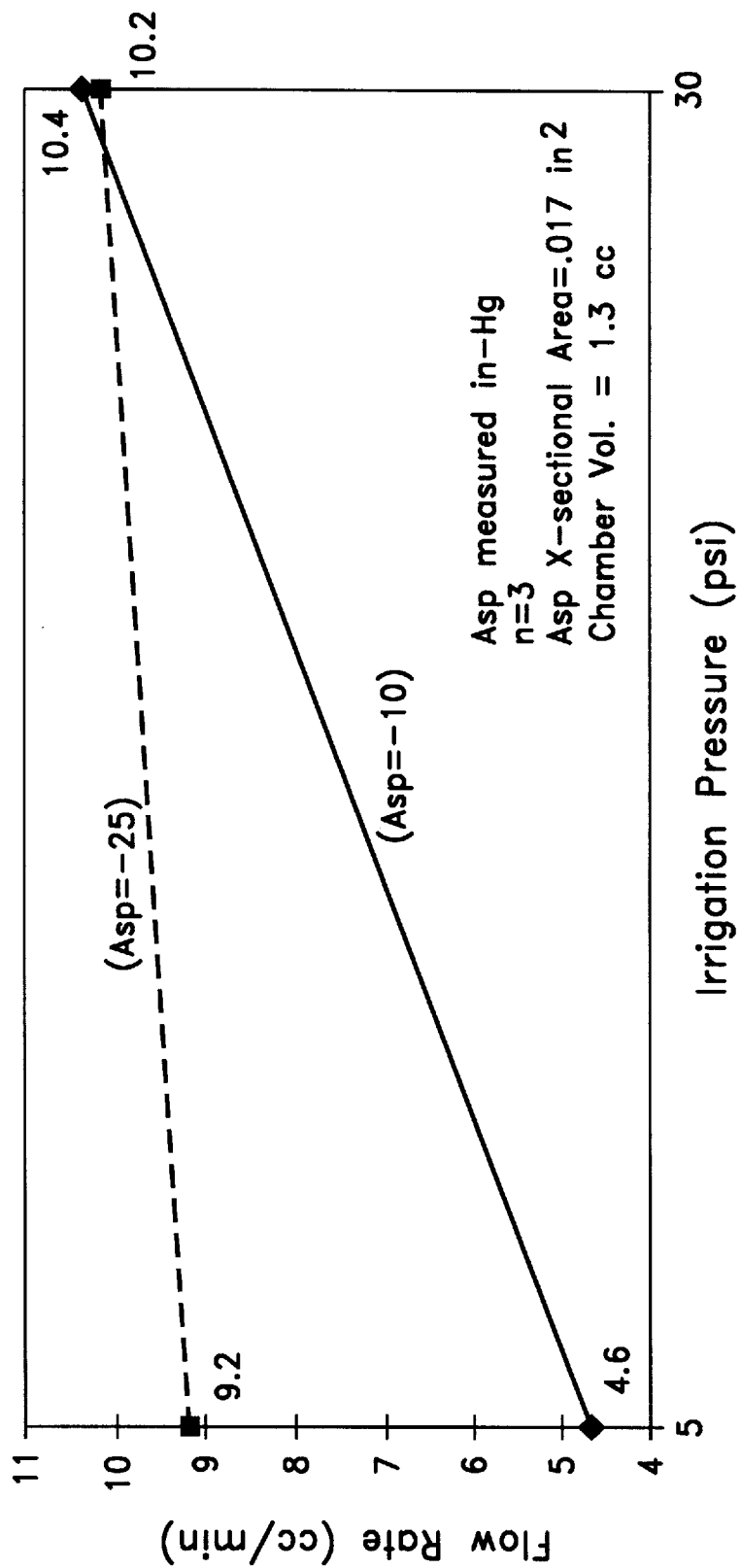
FIG. 2 is a graph illustrating the effect of irrigation and aspiration pressures on flow rate within the emboli containment chamber.

The analysis of the interaction between the irrigation and aspiration pressure showed that by using a lower aspiration pressure of −25 in-Hg the effect of the irrigation pressure can be minimized (see FIG. 2). The increase in the flow rate between 5 and 30 psig was 1.0 cc/min for an aspiration pressure of −25 in-Hg, whereas the increase was significantly higher, 5.6 cc/min, when an aspiration pressure of −10 in-Hg was used. Another advantage of using the lower aspiration pressure was that it took longer for the pressure to equalize as measured by the aspiration pressure gauge thus a higher flow rate was sustained over a longer period of time.

The tubular chamber used in this study was 4 mm×100 mm which contained a volume of 1.3 cc; therefore for the worst case flow rate of 4.6 cc/min (IP=5 psig, AP=−10 in-Hg) the fluid is exchanged approximately 3.5 times taking approximately 17 seconds for each exchange. The flow rate is approximately 9.2 cc/min for an IP=5 psig and an AP=−25 in-Hg, which would flush the 1.3 cc chamber in approximately 7.5 seconds or 8 times per minute.

This understanding of the fluid mechanics inside the emboli containment chamber resulting from the testing described above lead to the development of the method of the present invention, which provides efficient irrigation and aspiration for removal of emboli and debris inside the body following treatment of an occluded vessel.

Catheters of the Present Invention

The emboli containment system of the present invention comprises an inner catheter having an occlusive device at its distal end, a main catheter having an occlusive device at its distal end and an intermediate catheter. Separate irrigation and aspiration catheters can also be used if desired, either as a single catheter incorporating both or as two different devices.

Main Catheter

FIG. 3 illustrates a side view of a catheter which can be used as the outer or main catheter of the present system. Catheter 110 generally comprises an elongate flexible tubular body 116 extending between a proximal control end 112 and a distal functional end 114. The tubular body 116 has a main lumen 130 which extends between the ends 112 and 114. The main lumen 130 terminates in a proximal opening 123 and a distal opening 127. A smaller inflation lumen 132, configured in a side-by-side relationship with the main lumen 130, extends along the length of the tubular body 116, and terminates within an occlusion balloon 126 mounted on the distal end 114 of the catheter 110, as described below. The inflation lumen 132 is in fluid communication with the occlusion balloon 126, such that fluid passing through the inflation lumen 132 may be used to inflate or deflate the balloon 126. The proximal end of the inflation lumen 132 can terminate at one of the ports 122, 124 on the proximal end of the catheter 110.

A control manifold 119 is provided at the proximal end 112 of the catheter 110. The control manifold 119 is generally provided with a number of ports to provide access to the catheter lumen 130. For example, for the embodiment depicted in FIG. 3, the control manifold 119 is provided with a catheter end-access port 122 and a catheter side-access port 124, to provide an introduction point for the insertion of other catheters into the lumen 130. Ports 122 and 124 are preferably provided with standard Touhy Borst connectors, although other types of connectors may be used. An inflation port 118, in fluid communication with the small inflation lumen 132, is further provided on the manifold 119 for attachment of devices to inflate or deflate the occlusion balloon 126. The manifold 119 is also provided with an irrigation/aspiration port 120 which is in fluid communication with the lumen 130, for attachment of devices to provide irrigation fluid or aspiration pressure. Other embodiments of the main catheter 110 may feature more or less ports, depending upon the number of lumen in the catheter and the desired functionalities of the catheter.

The manifold 119 is preferably formed out of hard polymers or metals, which possess the requisite structural integrity to provide a functional access port to the catheter lumen, such as for balloon inflation or delivery of irrigation fluid and/or aspiration pressure. In one preferred embodiment, the manifold 119 is integrally formed out of polycarbonate. Of course, any suitable material may be used to form the manifold 119.

As illustrated in FIG. 3, an inflatable balloon 126 is mounted on the distal end 114 of the catheter 110. The inflatable balloon 126 will function as an occlusion balloon, to prevent blood and debris from passing through the blood vessel distal to the balloon 126. Thus, the inflatable balloon 126 is preferably able to expand to fit a variety of different blood vessel diameters. Accordingly, it is preferred that the inflatable balloon 126 have a compliant expansion profile, tending to increase in radial diameter with increasing inflation pressure. To achieve this, the balloon 126 may be made out of materials which impart such expansion characteristics, including elastomeric materials such as latex or irradiated polyethylene. In one preferred embodiment, the inflatable balloon 126 is formed out of a material comprising a block copolymer of styrene-ethylene-butylene-styrene, sold under the trade name C-FLEX. Further details as to balloons of this type are disclosed in our copending application entitled "Pre-Stretched Catheter Balloon" Ser. No. 08/812,876, filed on the same date as the present application currently pending, the entirety of which is incorporated by reference.

Intermediate Catheters

FIG. 6 is a side view of an irrigation catheter 140 or aspiration catheter which may be utilized as the intermediate catheter in the present invention. It should be understood that when an irrigation catheter is used for the intermediate catheter, aspiration occurs through the outer pathway between the intermediate and main catheters, while irrigation occurs through the inner pathway. Similarly, when an aspiration catheter is used, aspiration occurs through the inner pathway while irrigation occurs through the outer pathway. Irrigation fluid is supplied under pressure at the proximal end of the catheter 142 and injected into the containment chamber through the side holes 146 and through the distal end of the catheter 144. Alternatively, aspiration pressure can be provided at the proximal end of the catheter 142 and fluid and debris aspirated through the side holes 146 and through the distal end of the catheter 144. The catheter 140 can be about 125 cm in length and constructed from a plastic material such as HYTREL tubing or high density polyethylene (HDPE) or PEBAX (Atochem, France). In order to achieve a softer distal section, the durometer of the tube 148 material is reduced in the distal section to about 55 whereas that of the proximal section 142 is higher, such as about 80. Proximal valves and fittings which are well known in the art can be mounted on the irrigation catheter 140 of FIG. 6.

FIGS. 7–10 illustrate another type of irrigation or aspiration catheter 230 a single operator catheter, which can be used as the intermediate catheter of the present system. In the case of the irrigation catheter, irrigation is through the inner pathway and aspiration is through the outer pathway. If the catheter is used for aspiration, aspiration is through the inner pathway and irrigation is through the outer pathway. As shown in FIGS. 7–10, the catheter 230 has an adaptor 232 on its proximal end. This single operator catheter 230 further comprises a long tubular body 236 having a distal end 238. The distal tip 238 can include a radiopaque marker to aid in locating the tip 238 during insertion into the patient, and is preferably soft to prevent damage to the patient's vasculature. At the distal end of the shaft 238, an inner catheter lumen 240 is attached. This lumen 240 provides a separate lumen, apart from the main irrigation or aspiration lumen 242 of the catheter 230, for the insertion of the inner catheter, and has an inner diameter sized to received the inner catheter. In a preferred embodiment, the inner diameter of the lumen is about 0.016 in to about 0.020 in, and more preferably is about 0.019 in. This inner catheter or guidewire lumen can be as short as 5 cm, but can extend 30 cm or longer in a proximal direction. During delivery of the catheter 230, the proximal end of the inner catheter is inserted into the distal end of the inner catheter lumen 240, and the lumen 240 is slidably advanced over the inner catheter. Only a short segment of the single operator catheter 230 rides over the inner catheter, and the inner catheter remains in the lumen 240 and does not enter the main lumen 242 of the catheter 230.

Although the inner catheter lumen 240 is shown in FIG. 7 as being located only on the distal end 238 of the shaft of the catheter 236, the lumen 240 can also be made to extend the entire length of the shaft 236 if desired. In both embodiments, the main lumen 242 is advantageously left completely unobstructed to provide more efficient irrigation or aspiration. The inner catheter lumen 240 can also include a slit 241 or weakened area in the outside wall of the lumen 240 along the entire length of the lumen 240 to facilitate faster and easier insertion and removal of the inner catheter through the side wall of the lumen 240. By inserting and removing the inner catheter through the side wall of the lumen 240 on the catheter 236, the need to remove adapters and attachments from the proximal end prior to slidably advancing or removing the catheter 236 over the inner catheter is eliminated. It should be understood that this slit 241 or weakened area through which the inner catheter can be inserted and removed can exist on the intermediate catheter regardless of whether the catheter is used for irrigation, aspiration, therapy or some other purpose.

FIG. 10A is a cross-sectional view of a single operator intermediate catheter 252 positioned within the main catheter 250. The separate lumen 254 adapted to receive the inner catheter is positioned adjacent the lumen of the intermediate catheter 252. It should be understood that this positioning will occur when any single operator intermediate catheter is used. FIG. 10A illustrates schematically the inner (IP) and outer pathways (OP) for irrigation and aspiration which are formed by the catheter system of the present invention when a single operator intermediate catheter is used.

Figure 11:
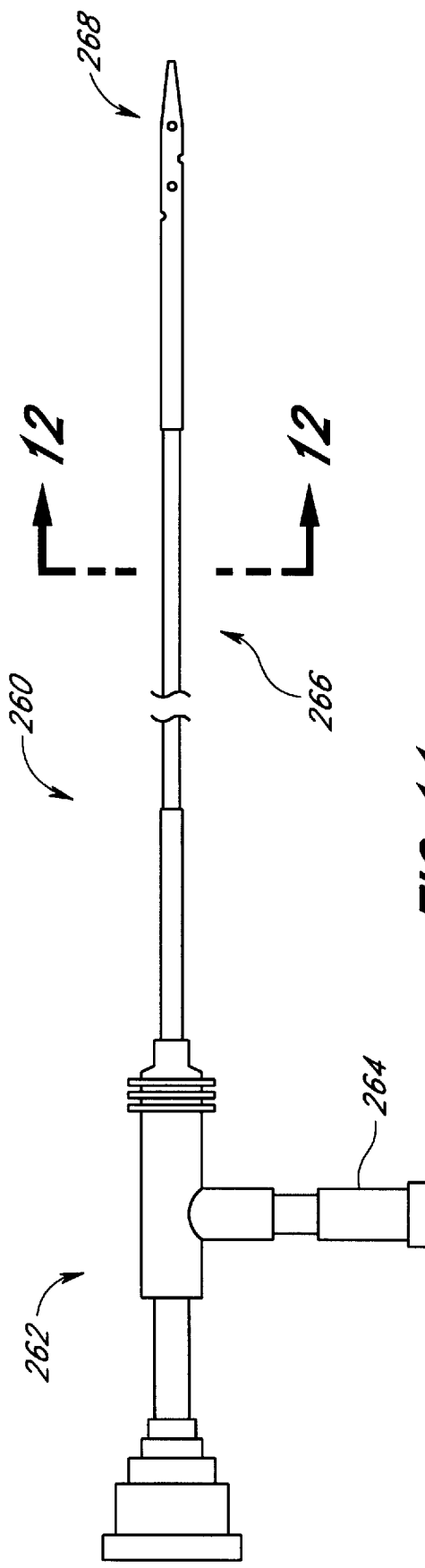
FIG. 11 is a side view of an over-the-wire aspiration catheter for use in the present invention.
Figure 13:
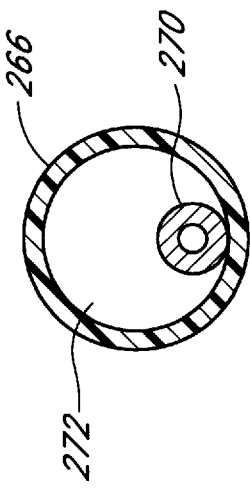
FIG. 13 is a cross-sectional view of the over-the-wire aspiration catheter taken along line 12—12 in FIG. 11, showing a guidewire inserted therethrough.
Figure 12:
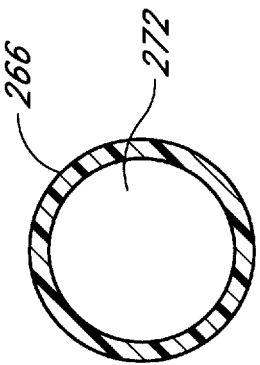
FIG. 12 is a cross-sectional view of the over-the-wire aspiration catheter taken along line 12—12 in FIG. 11.

An embodiment of an aspiration catheter suited for use as the intermediate catheter in the present invention is illustrated in FIGS. 11–13. The catheter 260 includes an adaptor 262, preferably a female luer adaptor, at its proximal end. The catheter 260 further includes an aspiration port 264 to which a source of negative pressure is attached. The aspiration catheter further comprises a long tubular body 266 having a distal end 268. The distal tip 268 can include a radiopaque marker to aid in locating the tip 268 during insertion into the patient, and is preferably soft to prevent damage to the patient's vasculature. The aspiration catheter is preferably about 145 cm in length, although this length can be varied as desired.

As seen in FIG. 12, the catheter body 266 is hollow, with an internal diameter sized to allow aspiration of emboli and debris. Preferably, the inner diameter ranged from about 0.020 in to about 0.050 in, and is preferably about 0.045 in. During insertion of this aspiration catheter 260, the proximal end of the inner catheter 270 is inserted into the distal end of the aspiration catheter 268, and the aspiration catheter 260 is slidably advanced over the inner catheter 270, which is positioned inside the hollow lumen 272 of the aspiration catheter 260. The position of the inner catheter 270 relative to the body of the aspiration catheter 266 is illustrated in FIG. 13, but of course, can vary. For this type of aspiration catheter 260, a very long inner catheter 270, generally around 300 cm in length, is used to facilitate the insertion of the aspiration catheter 260.

Figure 14:
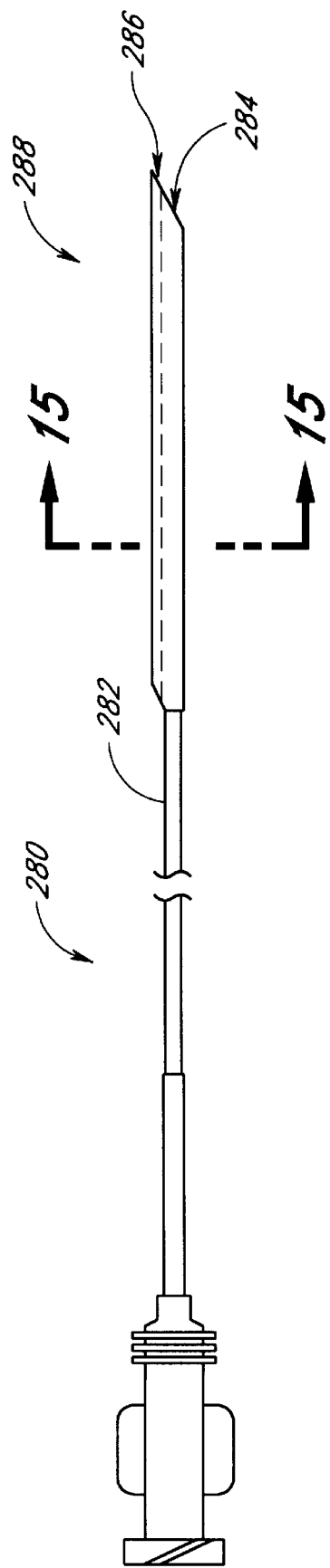
FIG. 14 is a side view of a single operator aspiration catheter for use in the present invention.
Figure 15:
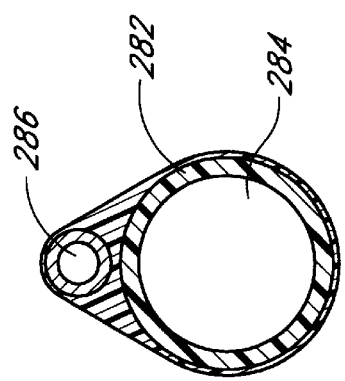
FIG. 15 is a cross-sectional view of the single operator aspiration catheter taken along line 15—15 in FIG. 14.

FIGS. 14–15 illustrate another embodiment of an aspiration catheter 250, a single operator catheter, suitable for use as an intermediate catheter in the present invention. This catheter 280 comprises an elongate shaft 282 with a lumen 284 for aspiration. At the distal end 288, a separate inner catheter lumen 286 is positioned adjacent the main aspiration lumen 284. Again, this lumen 286 provides a separate lumen, apart from the main lumen 284 of the catheter 280, for the insertion of the inner catheter. This inner catheter or guidewire lumen 286 can be as short as 5 cm, but can extend 30 cm or longer in a proximal direction. During delivery of the single operator aspiration catheter 280, the proximal end of the inner catheter is inserted into the distal end of the inner catheter lumen 286, and the lumen 286 is slidably advanced over the inner catheter. Only a short segment of the single operator aspiration catheter 280 rides over the inner catheter, and the inner catheter remains in the lumen 286 and does not enter the aspiration lumen 284 of the catheter 280. Again, the lumen 286 can have a slit (not shown) or weakened area in a side wall to facilitate insertion and/or removal of the inner catheter through the side wall of the lumen.

If desired, a rheolitic device such as the ANGIOJET thrombectomy catheter available from Possis Medical Inc., Minneapolis Minn. can be used. This device acts as both a therapy catheter and an aspiration catheter. The device breaks up the thrombus or other occlusion and removes it. This eliminates the need to provide separate catheters for these functions. Thus, the term "aspiration catheter" includes rheolitic devices and any device which creates an area of fluid turbulence and uses negative pressure to aspirate fluid and debris, and includes devices which create a venturi effect within the vessel.

Alternatively, a single catheter having two separate lumens can be used to provide both irrigation and aspiration. The dual lumen catheter can be configured to be over-the-wire, or of single operator design. Preferably, one lumen extends past the distal end of the catheter so that the opening of one lumen is spaced some distance apart from the opening of the second lumen. Thus, irrigation occurs some distance away from aspiration.

In another embodiment, a combined aspiration/therapy catheter can be used. For example, an angioplasty balloon can be attached to the distal end of an aspiration catheter. Alternatively, the aspiration catheter can be designed to deploy a stent within the occluded vessel, or the catheter could include an atherectomy device on its distal end. The aspiration and therapy devices are therefore delivered into the blood vessel together.

Inner Catheter

Figure 16:
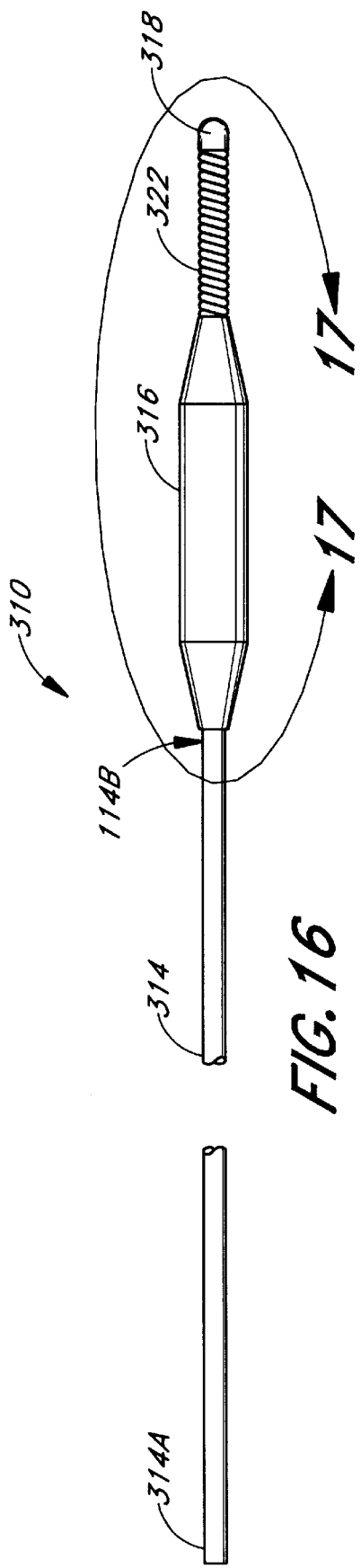
FIG. 16 is a side view of an inner catheter for use in the present invention.
Figure 17:
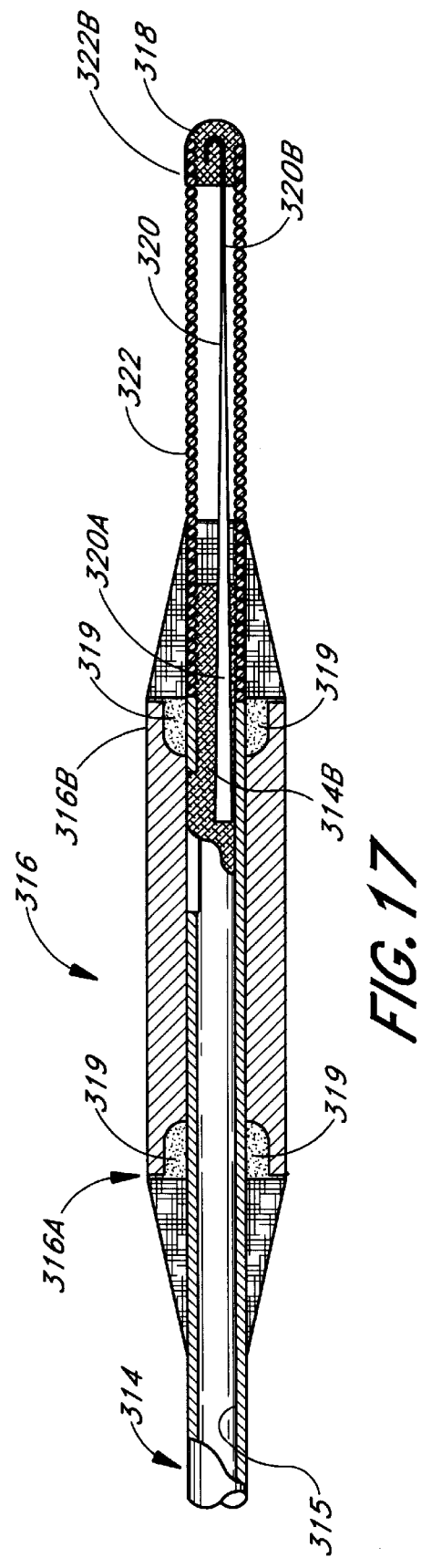
FIG. 17 is a partial cross-sectional view of the inner catheter taken along line 17—17 of FIG. 16.

As shown in FIGS. 16–17, the inner catheter apparatus 310 can generally be comprised of four communicating members including an elongated tubular member 314, a balloon member 316 and a core-wire member 320 and a coil member 322. The catheter apparatus 310 is preferably provided with an outer coating of a lubricous material, such as Teflon.

The body tubular member 314 of the catheter apparatus 310 is in the form of hypotubing and is provided with proximal and distal ends 314A and 314B and as well as an inner lumen 315 extending along the tubular member 314. The balloon member 316 is coaxially mounted on the distal end 314B of the tubular member 314 by suitable adhesives 319 at a proximal end 316A and a distal end 316B of the balloon member 316 as in the manner shown in FIG. 17. The core-wire member 320 of the catheter 310 may be comprised of a flexible wire 320. The flexible wire 320 is joined by soldering, crimping, or brazing at a proximal end 320A of the flexible wire 320 to the distal end 314B of the tubular member 314 as in the manner show in FIG. 17.

Preferably, the proximal end 320A of the flexible wire 320 has a transverse cross sectional area substantially less than the smallest transverse cross-sectional area of the inner lumen 315 of the tubular member 314. In the preferred embodiment, the flexible wire 320 tapers in the distal end 320B to smaller diameters to provide greater flexibility to the flexible wire 320. However, the flexible wire may be in the form of a solid rod, ribbon or a helical coil or wire or combinations thereof.

As shown in FIG. 17, the distal end 320B of the flexible wire 320 is secured to a rounded plug 318 of solder or braze at the distal end 322B of the coil member 322. The coil member 322 of the catheter 310 may be comprised of a helical coil 322. The coil member 322 is coaxially disposed about the flexible wire 320, and is secured to the flexible wire 320 by soldering or brazing at about the proximal end 320A of the flexible wire 320 as in the manner shown in FIG. 17. The balloon member 316 is preferably a compliant balloon formed of a suitable elastic material such as a latex or the like. The flexible coil 322 is preferably formed of a radiopaque material such as platinum or gold. The flexible core-wire 320 and the tubular member 314 are preferably formed of a nickel-titanium alloy or stainless steel.

The catheters of the present invention are preferably provided with a coating on the outer surface, or on both the inner and outer surfaces. Suitable coatings include hydrophilic, hydrophobic and antithrombogenic coatings. Examples include heparin and TEFLON. These coatings can be applied using methods well known in the art.

Additional details relative to the catheters described above are found in copending applications Ser. Nos. 08/813,023 pending, 08/812,140 pending, 08/813,808 pending and 08/812,876 pending, filed on the same date as the present application, entitled "Catheter for Emboli Containment".

Emboli Containment Methods of the Present Invention

The operation and use of the emboli containment system utilizing the catheters of the present invention for treating occluded vessels will now be described in connection with an occlusion formed by a stenosis in a carotid artery, as illustrated in FIGS. 18A–F. It should be noted that this application is merely exemplary, and that the method of the present invention can be used in other blood vessels in the body as well. The word "proximal" as used herein refers to the portion of the catheter closest to the end which remains outside the patient's body, while "distal" refers to the portion closest to the end which is inserted into the body.

A guiding catheter (not shown) is first introduced into the patient's vasculature through an incision in the femoral artery in the patient's groin. The guide catheter is advanced through the artery into the aorta of the heart of the patient and into the ostium of the carotid artery to be treated, where it remains throughout the procedure if needed. Fluoroscopy is typically used to guide the catheter and other devices to the desired location within the patient. The devices are typically marked with radiopaque markings to facilitate visualization of the insertion and positioning of the devices.

Referring now to FIG. 18A, a main catheter 410 having a distal attached occlusive device 412, in this example an inflatable balloon, is advanced into the ostium of the carotid artery and into the lumen 418 of the vessel 414. The main catheter 410 with the occlusive device 412 thereon is advanced until the device 412 is just proximal to the stenosis 406. The device is activated, i.e. the balloon 412 is then inflated, to occlude the vessel 414. The inner catheter, in this example a guidewire 400, having an occlusive device 402, in this example an inflatable balloon, at its distal end 404 is next delivered through the main catheter 410. The occlusive device 402 is positioned just distal to the occlusion 406. The occlusive device is activated, i.e., the balloon 402 is inflated to create an isolated chamber within the vessel which surrounds the occlusion. The balloons 402, 412 are each progressively inflated until they engage the side wall of the vessel 414 to occlude the lumen 418. Preferably, the distance between the proximal end of the occlusive device on the guidewire 404 and the distal tip of the occlusive device on the main catheter 416 should be approximately 5–10 cm.

Figure 18C:
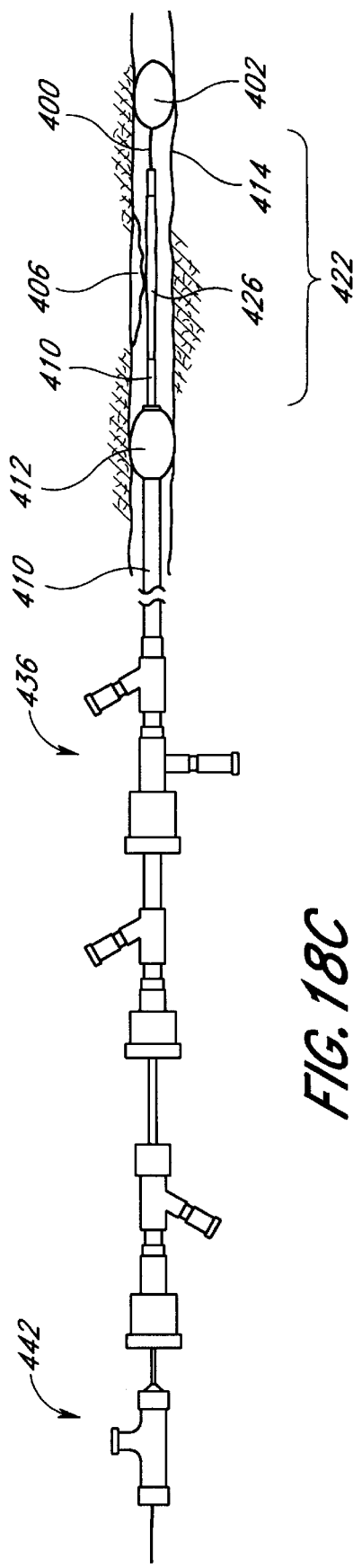

Advantageously, the present invention allows for the creation of a treatment and containment chamber whose length can be easily adjusted to isolate a specific area within a blood vessel. As soon as both balloons 402, 412 are inflated, a working space 422 is provided between the balloons 402, 412, so that therapeutic procedures can be undertaken to remove or reduce the occlusion 406 in the space between the balloons 422, without risk of unwanted particles or emboli escaping into the blood stream. The inner catheter 400 and the main catheter 410 with their attached distal occlusive devices 402, 412 are therefore used to create a chamber 422 surrounding the occlusion 406, and act to contain the emboli and debris 424 resulting from the treatment of the occlusion 406 as illustrated in FIG. 18C.

If desired, a third occlusive device can be delivered through the main catheter and deployed to occlude, for example, a branch or collateral vessel off the vessel being treated. This will ensure that the desired area within the vessel remains isolated during the treatment procedure.

Alternatively, a guide catheter or angiography catheter can first be delivered to the site of the occlusion. The inner catheter is inserted through the guide or angiography catheter, and positioned within the patient. The guide or angiography catheter is removed, and the main catheter is inserted over the inner catheter into position proximal to the occlusion. The occlusive device at the distal end of the main catheter is activated, the occlusive device on the inner catheter is put into position distal to the occlusion and activated, and the procedure continues as described above.

Alternatively, the main catheter can be delivered directly to a position just proximal to the occlusion, without use of a guide or angiography catheter. The inner catheter is then delivered through the main catheter as described above.

In another alternative embodiment of the present invention, the inner catheter can be delivered first through the guide catheter. The occlusive device on the distal end of the inner catheter is positioned distal to the occlusion. The main catheter is introduced over the inner catheter and advanced into the ostium of the carotid artery and into the lumen of the vessel. The main catheter is advanced until the balloon is just proximal to the occlusion. The intermediate catheter is then delivered into the chamber to provide appropriate therapy. The occlusive devices on the distal ends of the inner and main catheters are activated, to create a treatment and isolation chamber surrounding the occlusion. This method can be used when the physician determines that the risk of crossing the occlusion prior to activation of the proximal occlusive device is minimal.

Referring now to FIG. 18B, once the chamber has been created around the occlusion, an intermediate catheter 420 is delivered to the site of the occlusion 406. In the example illustrated in FIGS. 18A–F, the intermediate catheter 420 is a therapy catheter having an angioplasty balloon on its distal end. The intermediate catheter 420 is delivered to the site of the occlusion 406 as shown in FIG. 18B.

The term "therapy catheter" is meant to include any of a number of known devices used to treat an occluded vessel. For example, a catheter carrying an inflatable or mechanically activated balloon for use in balloon angioplasty, as is used in this example, can be delivered to dilate the stenosis. Thermal balloon angioplasty includes the use of heat to "mold" the vessel to the size and shape of the angioplasty balloon. Similarly, an intravascular stent can be delivered via a balloon catheter and deployed at the site of the stenosis to keep the vessel open. Cutting, shaving, scraping, or pulverizing devices can be delivered to excise the stenosis in a procedure known as atherectomy. A laser or ultrasound device can also be delivered and used to ablate plaque within the vessel. Various types of rheolitic devices could be used. Various thrombolytic or other types of drugs can be delivered locally in high concentrations to the site of the occlusion. It is also possible to deliver various chemical substances or enzymes via a catheter to the site of the stenosis to dissolve the obstruction. The catheter can also include a therapeutic device, such as an angioplasty balloon, and be capable of providing irrigation or aspiration through its main lumen. The term "therapy catheter" encompasses these and other similar devices.

Figure 18D:
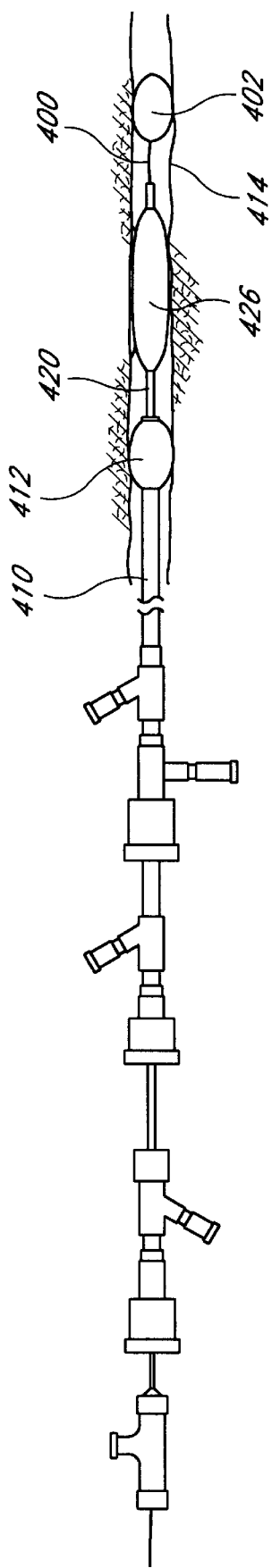

Referring now to FIG. 18D, after the balloons 402 and 412 are properly inflated, and the therapy catheter 420 in place, therapy begins. For emboli containment systems featuring balloon dilatation treatment, it is desired to compress the plaque or material forming the stenosis 406 to provide a larger passageway through the vessel. Thus, a balloon angioplasty catheter 420 is positioned such that the distal end with the balloon 426 thereon is at the site of the stenosis 406. When the balloon 426 has been properly positioned within the stenosis 406, the balloon 426 is inflated with a suitable inflation medium, as for example a radiopaque liquid. The angioplasty balloon 426 can be inflated to the desired pressure to cause compression of the plaque of the stenosis 406 against the sidewall of lumen 414 by the application of appropriate inflation pressure, as shown in FIG. 18D. As in conventional angioplasty procedures, the balloon 426 can be formed of a non-elastic relatively non-compliant material so that appropriate pressures, such as 10–15 atmospheres, can be created within the balloon to apply compressive forces to the vessel 414 without danger of rupturing the vessel 414. It should be appreciated that the non-elastic capabilities can also be achieved by a composite elastic material.

After appropriate therapy has been performed and the stenosis 406 has been removed or lessened using any of the methods and apparatus described above, the therapy balloon 426 is deflated as illustrated in FIG. 18E. A source of irrigation fluid (not shown) is connected to the adaptor 434 located at the proximal end of the therapy catheter 420, and a source of aspiration (not shown) is connected to an adaptor 436 located at the proximal end of the main catheter 410, as illustrated in FIG. 18F. Preferably, the source of irrigation fluid is a bag of normal saline, typically used in intravenous infusion. The source of aspiration is preferably a syringe. After the source of irrigation and aspiration are connected, irrigation and aspiration are begun. Irrigation fluid is provided through the inner pathway between the therapy catheter 420 and the guidewire 400, while aspiration is provided through the outer pathway between the therapy catheter 420 and the main catheter 410 as shown by the small arrows in FIG. 18F. Of course it is to be understood that irrigation fluid could be provided through the outer pathway while aspiration is provided through the inner pathway. In either case, suitable pressures are provided to ensure that the change in pressure inside the chamber does not damage the vessel. The change in pressure as fluid flows into and out of the chamber should not exceed about 50 psi. Suitable negative pressures range from approximately –10 to –30 in-Hg for aspiration, and irrigation pressure is about 5 to 30 psig. Note that these pressures are measured at the proximal end of the catheters.

In an alternative embodiment not shown, after therapy has been performed to remove or reduce the stenosis, the therapy catheter is removed from the emboli containment system, and an irrigation catheter is delivered to the emboli containment chamber. The irrigation catheter is inserted through the main catheter lumen. The main lumen of the irrigation catheter can ride over the inner catheter, or the inner catheter can be positioned in a separate lumen adjacent to the main lumen. The distal end of the irrigation catheter is positioned just proximal the distal occlusion balloon, preferably approximately 2 cm from the balloon. As noted above, the irrigation and main catheter are sized such that the irrigation catheter can pass through the main catheter lumen and the annulus or outer pathway between the main catheter lumen and the irrigation catheter is large enough to allow aspiration of the blood and debris within the chamber through it. Irrigation fluid is provided through the inner pathway between the inner catheter and the irrigation catheter. Alternatively, an aspiration catheter, or similar debris removing device, can be used as the intermediate catheter. In this embodiment of the invention, the aspiration catheter is delivered in the same manner as described above for the irrigation catheter. Aspiration then occurs through the inner pathway, while irrigation is provided through the outer pathway.

Once the desired catheters are properly positioned, irrigation and aspiration are performed. The irrigation fluid and aspiration are delivered in such a way as to ensure that the change of pressure within the chamber is below about 50 psi to avoid damaging the vessel. The irrigation fluid, preferably normal saline solution, is preferably delivered at a pressure of from about 5 psi to about 50 psi; 5 psi is preferred. The aspiration pressure is preferably between about –5 and –30 in-Hg, and more preferably is about –20 in-Hg. Flow rates inside the chamber are optimal at 30 psi irrigation pressure and –10 to –25 in-Hg aspiration pressure. Again, these pressures are measured from at the proximal end of the catheters. The irrigation and aspiration can be delivered simultaneously, continuously, or delivery can be pulsed, or one can be delivered continuously while the other is delivered in a pulsed fashion. The user can determine the best method of delivery to provide optimized flow, turbulence, and clearance within the chamber.

Referring again to FIG. 18F, it is preferable that the inflation pressure within the distal occlusion balloon 402 is maintained at a level greater than the pressure in the chamber and the jet created by irrigation to avoid the leakage of fluid and debris past the distal occlusion balloon 402. Similarly, the inflation pressure in the proximal occlusion balloon 412 should be maintained at a level greater than the pressure in the chamber and the aspiration pulsation to avoid having fluid aspirated from behind the balloon 412 and possibly aspirating the balloon 412 itself. Again, the irrigation and aspiration pressures provided are such that the change in pressure during fluid flow into and out of the vessel does not damage the vessel. The change in pressure is preferably no greater than about 50 psi.

Figure 18G:
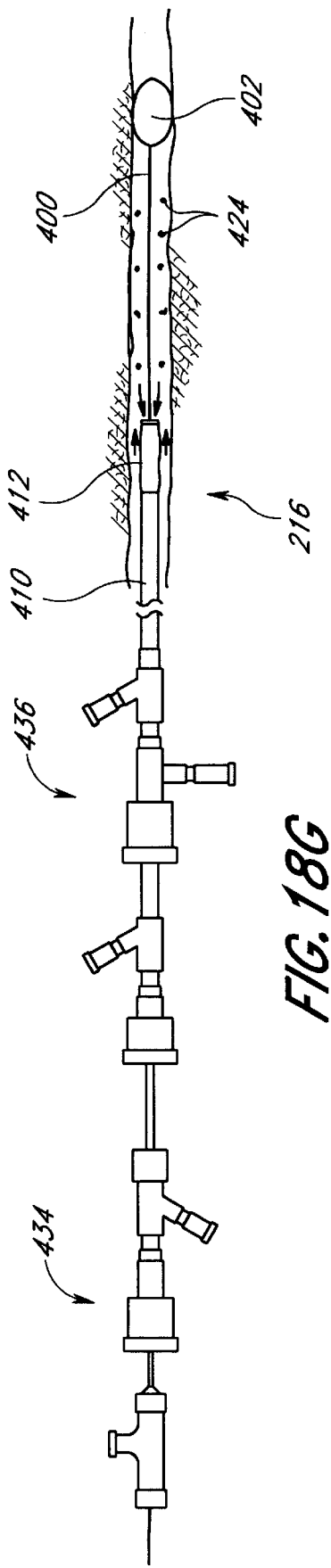

In another embodiment of the present invention, after the therapy catheter is removed, the aspiration catheter is delivered such that its distal end is positioned approximately 1–2 cm from the distal occlusive device. The proximal occlusive device is then deactivated, to allow blood flow into the chamber. This blood flow is used as irrigation flow. The blood, acting as irrigation fluid, is aspirated together with particles and debris through the aspiration catheter. This eliminates the need for a separate source of irrigation fluid. In this embodiment, it is preferred that the blood flow rate in the vessel is greater than about 100 cc/min, and flow rates of 60–80 cc/min are preferred. This method is illustrated in FIG. 18G.

Figure 18H:
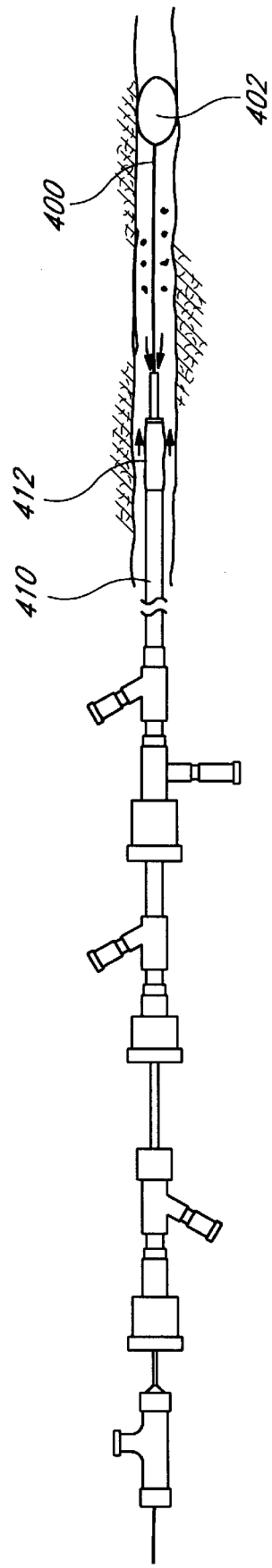

In yet another embodiment, illustrated in FIG. 18H, after the therapy catheter is removed, the proximal occlusive device is deactivated, allowing blood flow into the chamber.

The blood, acting as irrigation fluid, is aspirated together with particles and debris through the opening in the main catheter. This eliminates the need for a separate aspiration catheter and a separate source of irrigation fluid, thereby reducing the time necessary to complete the procedure.

Aspiration and irrigation are continued until particles and debris 424 are removed from the chamber 422, then the irrigation, aspiration, or the therapy catheter 420, is removed. First the distal 402 and then the proximal 412 occlusion balloons are deflated, and the guidewire 400 and main catheter 410 are removed. Finally, the guide catheter is removed, and the incision in the patient's femoral artery is closed.

Although the foregoing detailed description has described several embodiments of the present invention, it is to be understood that the above description is illustrative only and not limiting of the disclosed invention. It will be appreciated that certain variations of the present invention may suggest themselves to those skilled in the art. Thus, the spirit and scope of this invention are to be limited only by the claims which follow.

What is claimed is:

1. A method for containing and removing an occlusion within a blood vessel comprising:
    creating a chamber within said vessel between at least two occlusive devices positioned on either side of said occlusion, said chamber being of adjustable length; and
    providing irrigation fluid at one end of said chamber while providing aspiration at the other end of said chamber, creating a pressure change within said chamber that does not exceed about 50 psi.

2. The method of claim 1, wherein proximal aspiration pressure is between about −10 and −30 in-Hg, and said irrigation fluid is provided at a proximal pressure of between about 5 and 30 psig.

3. The method of claim 1, wherein said chamber is created between two inflatable balloons.

4. The method of claim 1, wherein said vessel is less than about 25 mm in diameter.

5. The method of claim 1, wherein said vessel is about 6 mm in diameter.

6. The method of claim 1, wherein said aspiration and said irrigation fluid are delivered simultaneously.

7. The method of claim 1, wherein said aspiration is delivered in a discontinuous manner.

8. The method of claim 1, wherein said irrigation fluid is delivered in a discontinuous manner.

9. A method for treating an occlusion and containing and removing emboli and debris from within a blood vessel comprising:
    delivering a main catheter having a first occlusive device on a distal end through said blood vessel until said occlusive device is proximal to said occlusion;
    activating said first occlusive device;
    delivering an inner catheter having a second occlusive device on a distal end through said blood vessel and across said occlusion until said second occlusive device is distal to said occlusion;
    activating said second occlusive device;
    delivering an intermediate catheter through said blood vessel until said intermediate catheter is at said occlusion;
    performing therapy on said occlusion using said intermediate catheter;
    providing irrigation fluid adjacent one of the occlusive devices while providing aspiration adjacent the other occlusive device to remove said occlusion and said emboli and debris, creating a pressure change within the vessel that does not exceed about 50 psi.

10. The method of claim 9, further comprising delivering a third occlusive device through said blood vessel to occlude a branch off said blood vessel.

11. The method of claim 9, further comprising the step of sizing said inner catheter and said intermediate catheter to provide an annulus therebetween, and wherein said irrigation fluid is provided through said annulus.

12. The method of claim 9, further comprising the step of sizing said intermediate catheter and said main catheter to provide an annulus therebetween, and wherein said aspiration is provided through said annulus.

13. The method of claim 9, further comprising the step of sizing said inner catheter and said intermediate catheter to provide an annulus therebetween, and wherein said aspiration is provided through said annulus.

14. The method of claim 9, further comprising the step of sizing said intermediate catheter and said main catheter to provide an annulus therebetween, and wherein said irrigation fluid is provided through said annulus.

15. The method of claim 9, wherein said inner catheter is a guidewire.

16. The method of claim 9, wherein at least a portion of said main catheter rides over said inner catheter during said delivery step.

17. The method of claim 9, wherein at least a portion of said intermediate catheter rides over said inner catheter during said delivery step.

18. The method of claim 9, further comprising the steps of removing said therapy catheter, deactivating said second occlusive device and removing said inner catheter, and deactivating said first occlusive device and removing said main catheter following the step of providing irrigation fluid and aspiration.

19. The method of claim 9, wherein said first and second occlusive devices are inflatable balloons, and the activating steps comprise inflating said balloons.

20. The method of claim 9, further comprising the step of removing said intermediate catheter following said performing therapy step, and delivering an irrigation catheter into said chamber, such that said irrigation fluid is provided through said irrigation catheter.

21. The method of claim 9, further comprising the step of removing said intermediate catheter following said performing therapy step, and delivering an aspiration catheter into said chamber, such that said aspiration is provided through said aspiration catheter.

22. A method for treating an occlusion and containing and removing emboli and debris from within a blood vessel comprising;
    delivering an inner catheter having a first occlusive device on a distal end through said blood vessel until said first occlusive device is proximal to said occlusion;
    delivering a main catheter having a second occlusive device on a distal end through said blood vessel until said second occlusive device is proximal to said occlusion;
    activating said second occlusive device;
    positioning said first occlusive device distal to said occlusion;
    activating said first occlusive device;
    delivering an intermediate catheter through said blood vessel until said intermediate catheter is at said occlusion;

performing therapy on said occlusion using said intermediate catheter to reduce said occlusion;

providing irrigation fluid adjacent one of the occlusive devices while providing aspiration adjacent the other occlusive device to remove said occlusion and said emboli and debris, creating a pressure change within the vessel that does not exceed about 50 psi.

23. The method of claim 22, further comprising the step of sizing said inner catheter and said intermediate catheter to provide an annulus therebetween, and wherein said irrigation fluid is provided through said annulus.

24. The method of claim 22, further comprising the step of sizing said intermediate catheter and said main catheter to provide an annulus therebetween, and wherein said aspiration is provided through said annulus.

25. The method of claim 22, further comprising the step of sizing said inner catheter and said intermediate catheter to provide an annulus therebetween, and wherein said aspiration is provided through said annulus.

26. The method of claim 22, further comprising the step of sizing said intermediate catheter and said main catheter to provide an annulus therebetween, and wherein said irrigation fluid is provided through said annulus.

27. The method of claim 22, wherein said vessel is less than about 25 mm in diameter.

28. The method of claim 22, wherein said first and second occlusive devices are inflatable balloons, and the activating steps comprise inflating said balloons.

29. The method of claim 22, further comprising the step of removing said intermediate catheter following said performing therapy step, and delivering an irrigation catheter into said chamber, such that said irrigation fluid is provided through said irrigation catheter.

30. The method of claim 22, further comprising the step of removing said intermediate catheter following said performing therapy step, and delivering an aspiration catheter into said chamber, such that said aspiration pressure is provided through said aspiration catheter.

31. A method for treating an occlusion and containing and removing emboli and debris from within a blood vessel comprising:

delivering an inner catheter having a first occlusive device on a distal end through said blood vessel until said first occlusive device is distal to said occlusion;

delivering a main catheter having a second occlusive device on a distal end through said blood vessel until said second occlusive device is proximal to said occlusion;

activating said first and second occlusive devices;

delivering an intermediate catheter through said blood vessel until said intermediate catheter is at said occlusion;

performing therapy on said occlusion using said intermediate catheter to reduce said occlusion;

providing irrigation fluid adjacent one of the occlusive devices while providing aspiration adjacent the other occlusive device to remove said occlusion and said emboli and debris, creating a pressure change within the vessel that does not exceed about 50 psi.

32. The method of claim 31, further comprising the step of sizing said inner catheter and said intermediate catheter to provide an annulus therebetween, and wherein said irrigation fluid is provided through said annulus.

33. The method of claim 31, further comprising the step of sizing said intermediate catheter and said main catheter to provide an annulus therebetween, and wherein said aspiration is provided through said annulus.

34. A method for treating an occlusion and containing and removing emboli and debris from within a blood vessel comprising:

delivering a main catheter having a first occlusive device on a distal end through said blood vessel until said occlusive device is proximal to said occlusion;

activating said first occlusive device;

delivering an inner catheter having a second occlusive device on a distal end through said blood vessel and across said occlusion until said second occlusive device is distal to said occlusion;

activating said second occlusive device to form a chamber within said blood vessel;

delivering an intermediate catheter through said blood vessel into said chamber to treat said occlusion, wherein said intermediate catheter creates a pressure change within said chamber which does not exceed 50 psi.

35. The method of claim 34, further comprising delivering a third occlusive device through said blood vessel to occlude a branch off said blood vessel.

36. The method of claim 34, wherein said inner catheter is a guidewire.

37. The method of claim 34, wherein at least a portion of said main catheter rides over said inner catheter during said delivery step.

38. The method of claim 34, wherein at least a portion of said intermediate catheter rides over said inner catheter during said delivery step.

39. The method of claim 34, wherein said first and second occlusive devices are inflatable balloons, and the activating steps comprise inflating said balloons.

40. The method of claim 34, wherein said intermediate catheter is a rheolitic device.

41. The method of claim 34, wherein said intermediate catheter comprises an angioplasty balloon attached to a catheter capable of providing irrigation or aspiration.

* * * * *